(12) United States Patent
Kobayashi (10) Patent No.: US 7,945,398 B2
(45) Date of Patent: May 17, 2011

(54) REFLOW PROCESS EVALUATION DEVICE AND REFLOW PROCESS EVALUATION METHOD

(75) Inventor: Yoko Kobayashi, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 6 days.

(21) Appl. No.: 12/331,946

(22) Filed: Dec. 10, 2008

(65) Prior Publication Data

US 2009/0164146 A1     Jun. 25, 2009

(30) Foreign Application Priority Data

Dec. 20, 2007  (JP) ................................ 2007-328161

(51) Int. Cl.
*G06F 19/00*    (2006.01)
(52) U.S. Cl. ............. 702/42; 702/43; 257/787; 438/127
(58) Field of Classification Search .................... 702/42, 702/43; 257/787; 438/127
See application file for complete search history.

(56) References Cited

FOREIGN PATENT DOCUMENTS

| JP | 2001-298107 A | 10/2001 |
| JP | 2001-358460 A | 12/2001 |
| JP | 2006-313127 A | 11/2006 |

OTHER PUBLICATIONS

Shinichi et al. Hitachi Ltd. JP 2006-313127.*

\* cited by examiner

*Primary Examiner* — Sujoy K Kundu
(74) *Attorney, Agent, or Firm* — Arent Fox LLP (57) ABSTRACT

A reflow process evaluation device includes, a stress calculation part for calculating an average principal stress acting on a joint portion, wherein a principal stress occurs when a chip and a substrate are joined by solder with a reflow method and a rupture occurrence ratio computation part for computing an occurrence ratio at which the joint portion ruptures based on a relational expression between the occurrence ratio and the average principal stress acting on the joint portion and the average principal stress calculated by the stress calculation part.

4 Claims, 9 Drawing Sheets

PERSPECTIVE VIEW

SIDE VIEW

FIG. 9

WIRING LAYER

WIRING LAYER AROUND HERE STRIPS

WIRING LAYER POSITION

WIRING LAYER

OCCURRENCE OF STRIPPING

ENLARGED VIEW OF WIRING LAYER PART

REFLOW PROCESS EVALUATION DEVICE AND REFLOW PROCESS EVALUATION METHOD

CROSS REFERENCES TO RELATED APPLICATIONS

This application is based upon and claims the benefit of priority from the prior Japanese Patent Application No. 2007-328161 filed on Dec. 20, 2007, the entire contents of which are incorporated herein by reference.

BACKGROUND

1. Field

An aspect of the invention relates to a reflow process evaluation device and a reflow process evaluation method for supporting and evaluating the design of a reflow process for mounting an LSI package.

2. Description of the Related Art

Figure 8:
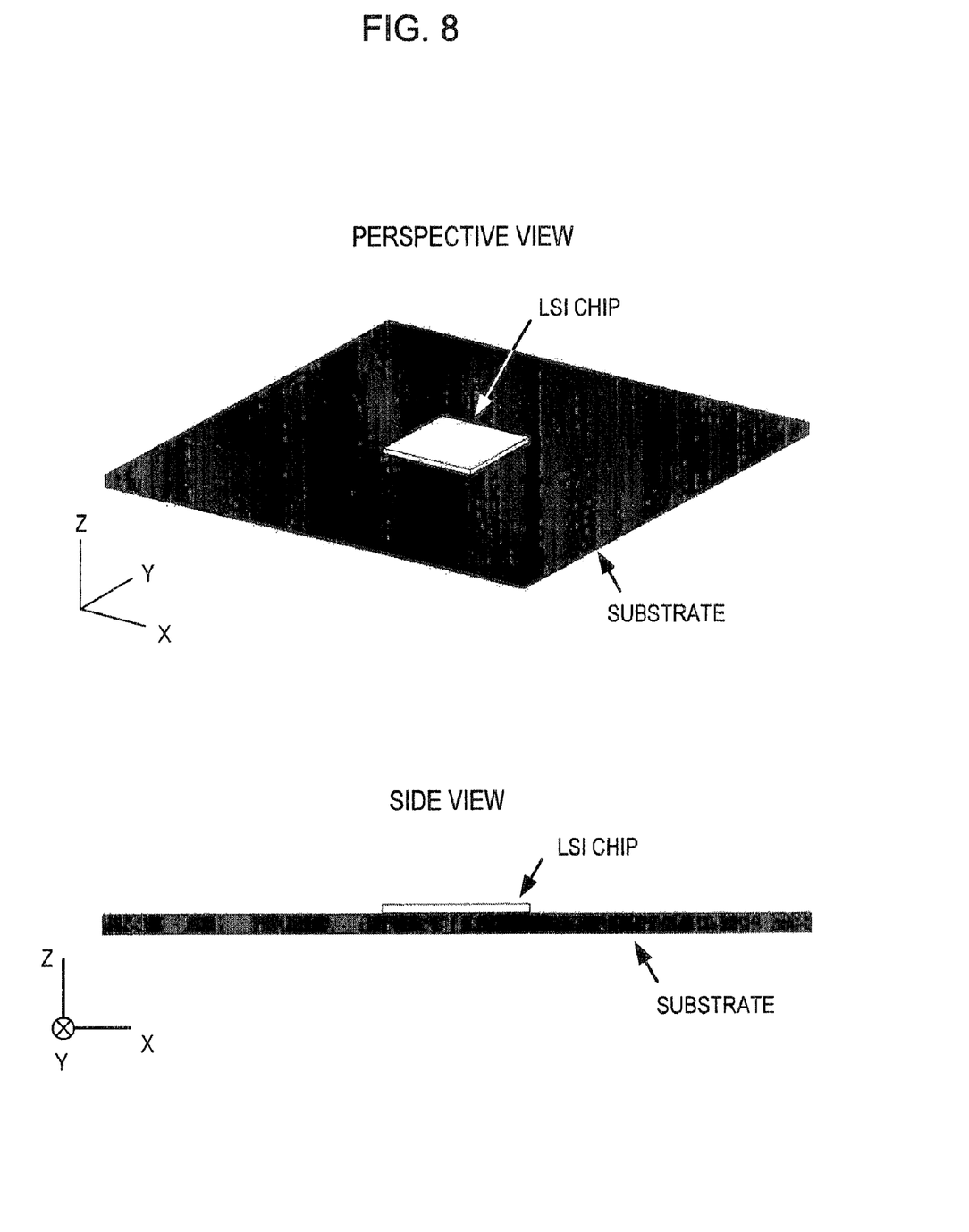
FIG. 8 is a perspective view and a side view showing the LSI chip and the substrate.
Figure 9:
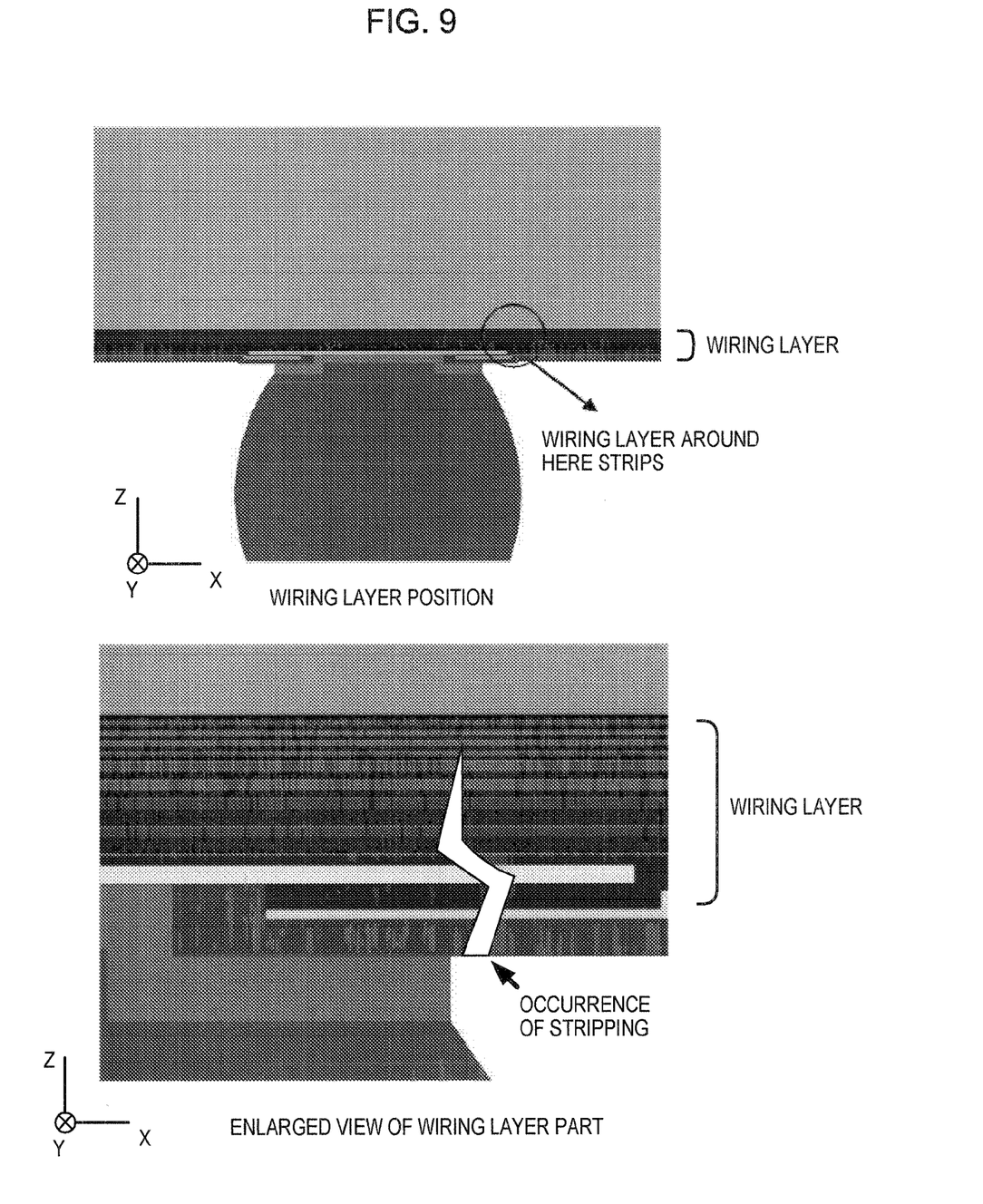
FIG. 9 is a view showing the position of a wiring layer on the LSI chip and an enlarged view of a stripping occurrence portion.

An LSI chip and a substrate are joined by soldering through a reflow method to treat the smaller size and higher density of the LSI chip, thereby manufacturing the LSI package. FIG. 8 shows a perspective view and a side view of the LSI chip and the substrate, and FIG. 9 shows an enlarged view of a wiring layer position and a wiring layer of the LSI chip. Owing to a thermal stress when soldering the LSI chip with the substrate, a joined solder portion on the side of the wiring layer of the LSI chip may be stripped (e.g., near the wiring layer in the enlarged view of FIG. 8), resulting in a significant problem in securing the reliability of the product.

As its countermeasure, there is a method for making the evaluation through a thermal stress simulation for evaluating the reliability against the stripping. In this evaluation method, the maximum stress on the overall chip is an evaluation index.

As shown in the prior art associated with this technology, a system for predicting the life of a solder joint more rapidly has been disclosed (e.g., patent document 1). Also, as shown in the prior art, an enhancement system capable of evaluating the optimal solder material and the component electrode constitution has been disclosed (e.g., patent document 2). Further, a failure occurrence prediction method and a highly reliable life estimation method for BGA subjected to a cold shock have been disclosed (e.g., patent document 3).

[Patent document 1] Japanese Laid-open Patent Publication No. 2006-313127
[Patent document 2] Japanese Laid-open Patent Publication No. 2001-358460
[Patent document 3] Japanese Laid-open Patent Publication No. 2001-298107

SUMMARY

According to an aspect of an embodiment of the present invention, a reflow process evaluation device includes, a stress calculation part calculating an average principal stress acting on a joint portion receiving a principal stress occurring when a chip and a substrate are joined by solder with a reflow method. The reflow process evaluation device further includes a rupture occurrence ratio computation part computing an occurrence ratio at which the joint portion ruptures based on a relational expression between the occurrence ratio and the average principal stress acting on the joint portion and the average principal stress calculated by the stress calculation part.

Additional objects and advantages of the invention will be set forth in part in the description which follows and, in part will be obvious from the description, or may be learned by practice of the present invention. The object and advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE EMBODIMENTS

Figure 1:
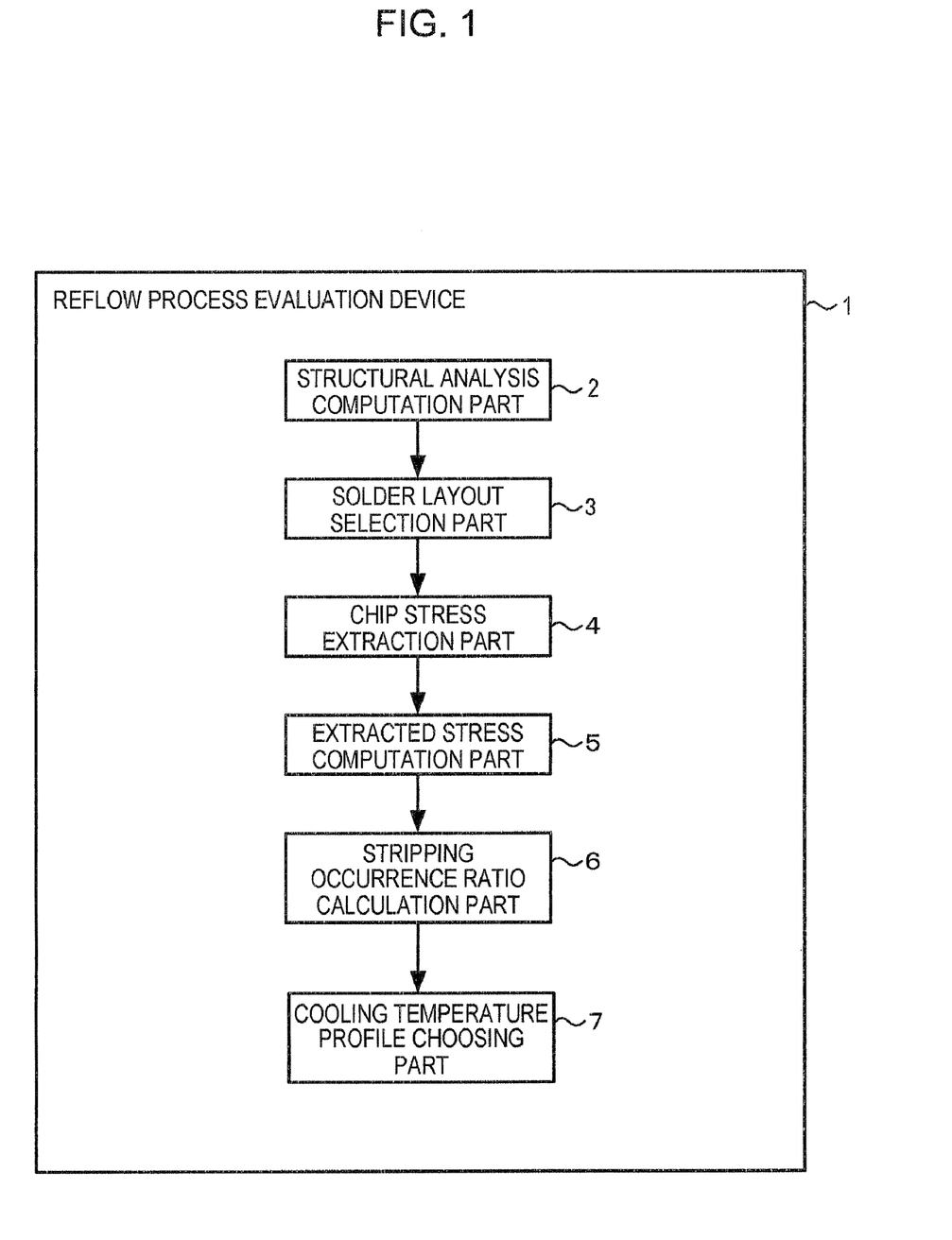
FIG. 1 is a block diagram showing one example of the configuration of a reflow process evaluation device according to an embodiment.

The embodiments of the present invention will be described below with reference to the drawings. First of all, a reflow process evaluation device according to an embodiment is shown in FIG. 1.

The reflow process evaluation device 1 according to an embodiment comprises a structural analysis computation part 2, a solder layout selection part 3, a chip stress extraction part 4, an extracted stress computation part 5, a stripping occurrence ratio calculation part 6, and a cooling temperature profile choosing part 7. The reflow process evaluation device 1 is a computer having the hardware resources such as a CPU, a memory, a hard disk drive, and an input/output unit Each of the above-mentioned parts is realized in cooperation with each hardware resource and software provided for the reflow process evaluation device 1.

The structural analysis computation part 2 computes the principal stress acting on the overall LSI chip in consideration of the model information or cooling temperature condition for the substrate or LSI chip, and the physical properties, such as a thermal expansion coefficient of material used in the substrate, LSI chip or solder. The solder layout selection part 3 selects a layout pattern adapted to the LSI chip or the substrate of an object from a plurality of predefined solder layout patterns (arrangement patterns), based on the model information of the substrate or LSI chip.

The chip stress extraction part 4 extracts only the principal stress acting on the stripping occurrence side element of the chip from the layout pattern selected by the solder layout selection part 3 and the computation result (principal stress acting on the overall LSI chip) by the structural analysis computation part 2. The extracted stress computation part 5 computes the principal stress (hereinafter an average principal stress) acting on one solder joint by averaging the principal stress extracted by the chip stress extraction part 4 by the number of electrodes joined by solder.

The stripping occurrence ratio calculation part 6 calculates the stripping occurrence ratio (rupture occurrence ratio) from the average principal stress calculated by the extracted stress computation part 5 according to a predetermined relational expression. The cooling temperature profile choosing part 7 chooses a predetermined temperature profile from a plurality of temperature profiles (hereinafter described) based on the stripping occurrence ratio calculated by the stripping occurrence ratio calculation part 6.

Figure 2:
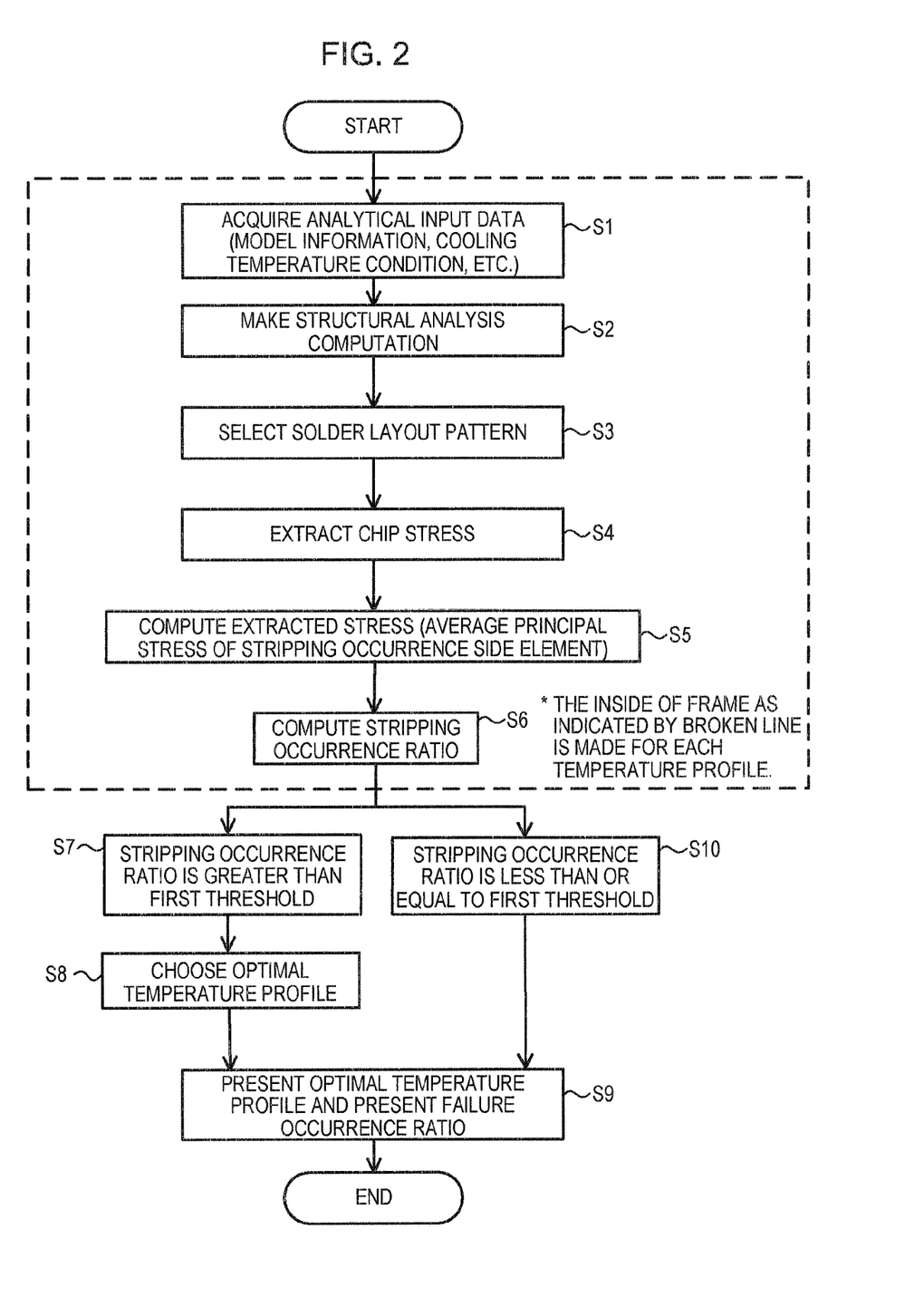
FIG. 2 is a flowchart showing one example of a process for the reflow process evaluation device according to an embodiment.

Referring to a flowchart of FIG. 2, a process for the reflow process evaluation device 1 according to this embodiment will be described below.

The structural analysis computation part 2 acquires analysis input data (model information of the LSI chip or substrate, cooling temperature condition of the LSI chip, or physical properties) (S1), and performs the structural analysis computation for computing the principal stress acting on the overall LSI chip (S2).

In a computation method for the principal stress, the structural analysis computation part 2 employs a time history stress (accumulated stress where the stress is accumulatively added with the passage of time based on the temperature profile) in the reflow. Hence, the structural analysis computation part 2 may adopt the principal stress at the final time when the time history stress is accumulated as the principal stress acting on the overall LSI chip. Since the final time is the time until a predetermined temperature (e.g., 25° C.) is reached, the structural analysis computation part 2 may adopt the principal stress accumulated until the predetermined temperature is reached, as the principal stress acting on the overall LSI chip. It should be noted that the maximum stress value halfway may be employed except for lead free solder.

The solder layout selection part 3 selects the layout pattern adapted to the LSI chip of an object from the plurality of predefined layout patterns, based on model information of the LSI chip (S3). Herein, one example of the layout pattern is shown in FIG. 3.

When the LSI chip and the substrate are joined by solder, the soldering is made not on the entire surface where both components are contacted with each other, but on the portion becoming the electrode. The solder joint portion (area where the substrate and the LSI chip are joined by solder) relies on the arrangement of electrodes in the LSI chip, but may differ depending on model information such as the kind or type number of LSI chip.

Figure 3:
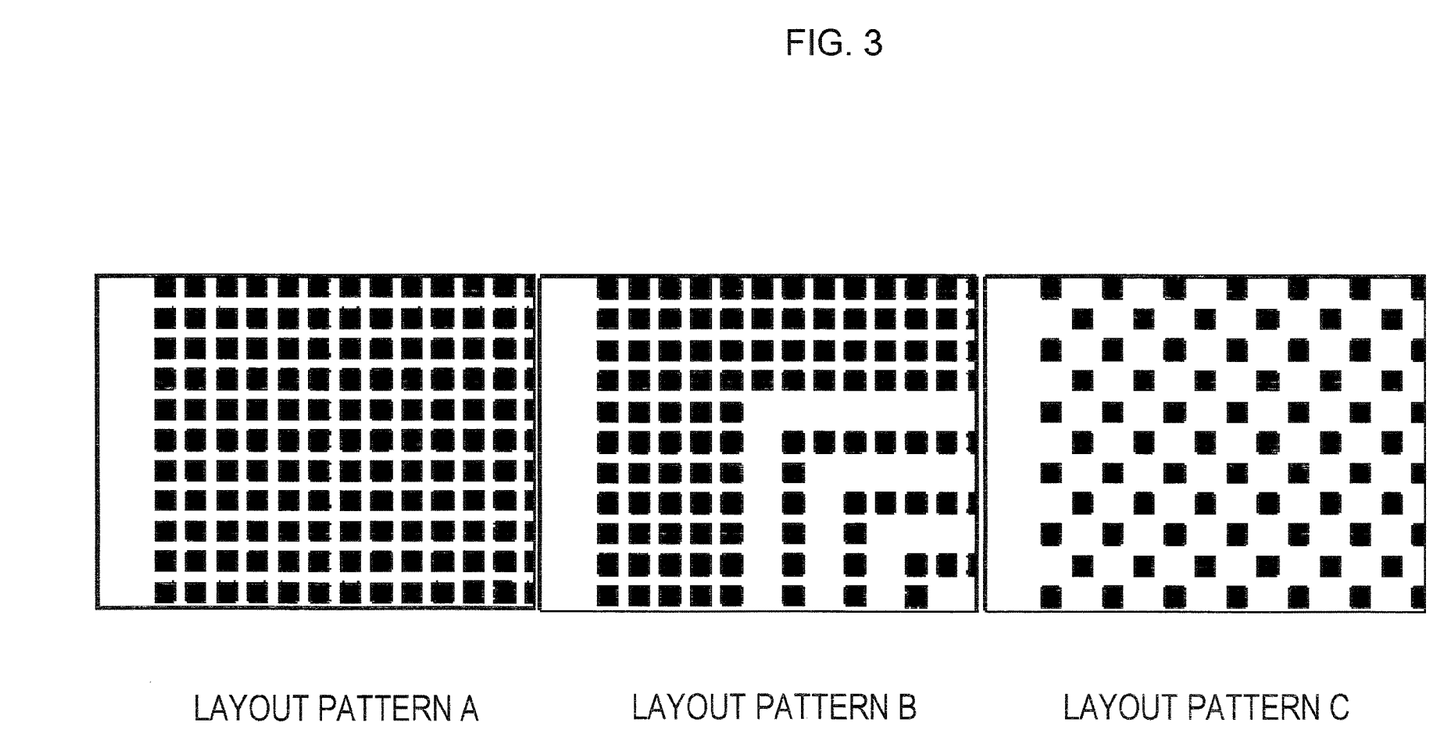
FIG. 3 is a view showing one example of a solder layout pattern according to an embodiment.

In FIG. 3, the solder joint portion is indicated in black. For example, the layout pattern A is the pattern in which the solder joint is evenly and densely made, and the layout pattern B is the pattern in which a dense section and a coarse section exist. The layout pattern C is the pattern in which the solder joint is made like dices (checkers).

Figure 4:
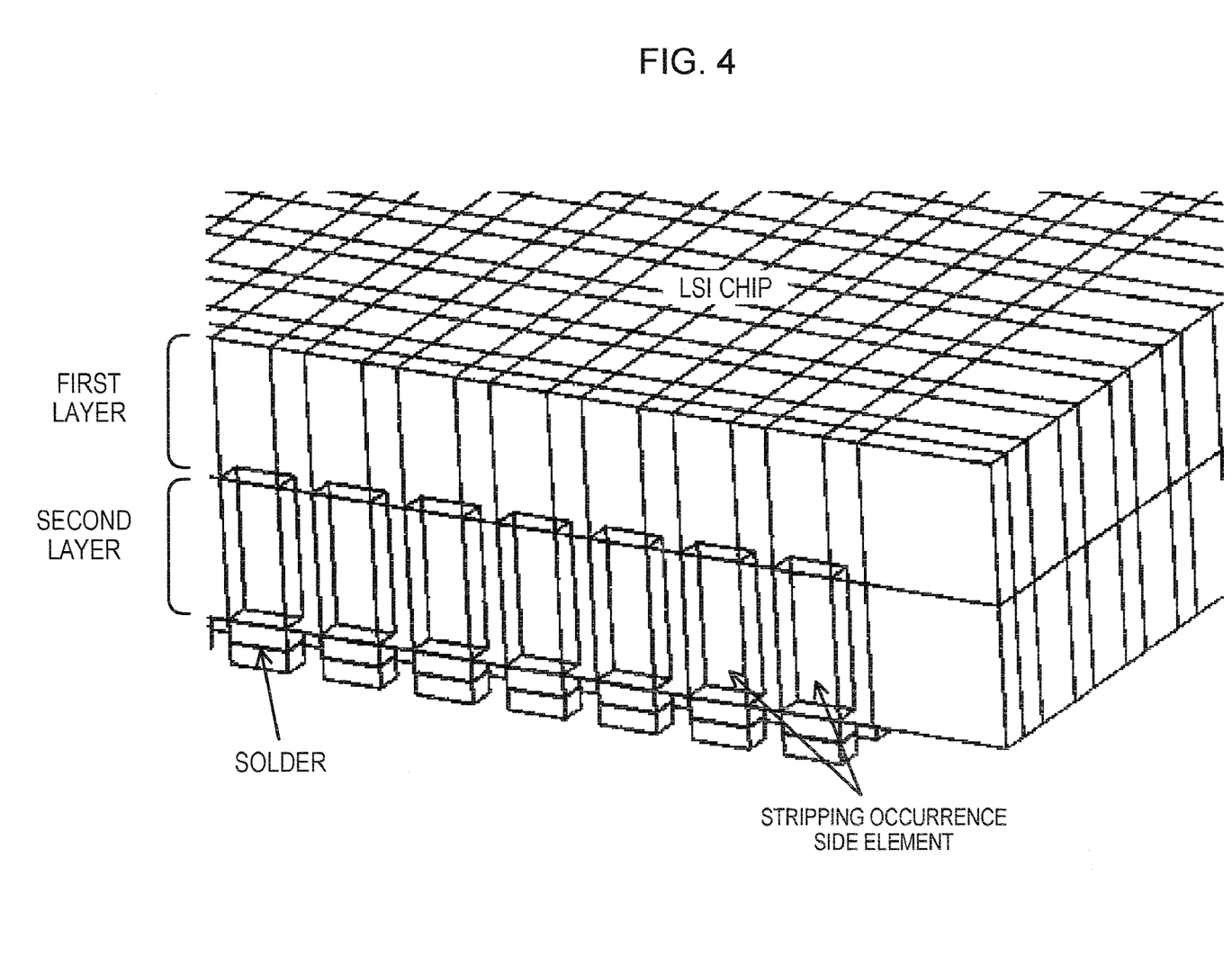
FIG. 4 is a view showing one example of a stripping occurrence side element according to this invention.

Then, the chip stress extraction part 4 extracts only the principal stress acting on the stripping occurrence side element (joint portion) of the chip from the layout pattern selected by the solder layout selection part 3 and the principal stress acting on the overall LSI chip by the structural analysis computation part 2 (S4). The stripping occurrence side element is the section susceptible to the principal stress occurring in making the solder joint. For example, in the case where the LSI chip is composed of two layers, a first layer and a second layer, where the second layer is joined with solder, as shown in FIG. 4, the stripping occurrence side element is in an area excluding the area of a portion (white portion in FIG. 3) other than the solder joint portion as indicated by the selected layout pattern in the area of the second layer.

The chip stress extraction part 4 calculates the principal stress acting on the stripping occurrence side element by using the principal stress acting on the entirety, and a ratio of the solder joint portion to the entire surface where the LSI chip and the substrate are contacted with each other.

In this way, the reflow process evaluation device 1 calculates the principal stress in accordance with the layout pattern with the arrangement of electrodes, provided that the stress acts on the entire area of the surface where the LSI chip and the substrate are contacted. In this way, a more accurate analysis result may be obtained.

Returning to the flowchart of FIG. 2, the extracted stress computation part 5 computes the average value of principal stress acting on one electrode (average value of principal stress acting on one section joined by solder, hereinafter referred to as an average principal stress) by averaging the principal stress acting on the stripping occurrence side element extracted by the chip stress extraction part 4 with the number of electrodes for solder joint (S5). In this embodiment, the extracted stress computation part 5 computes the average principal stress. The extracted stress computation part 5 may also calculate the standard deviation.

In this way, an effective parameter with the presence or absence of stripping occurrence as an evaluation index can be obtained by restricting the evaluation to the element in which stripping occurs, and converting the evaluated stress into the total average value.

The stripping occurrence ratio calculation part 6 calculates the stripping occurrence ratio from a relational expression between average principal stress and stripping occurrence ratio and the average principal stress calculated at S5 (S6). Herein, referring to FIG. 5, a method for obtaining the relational expression between the average principal stress and the stripping occurrence ratio will be described below.

Figure 5:
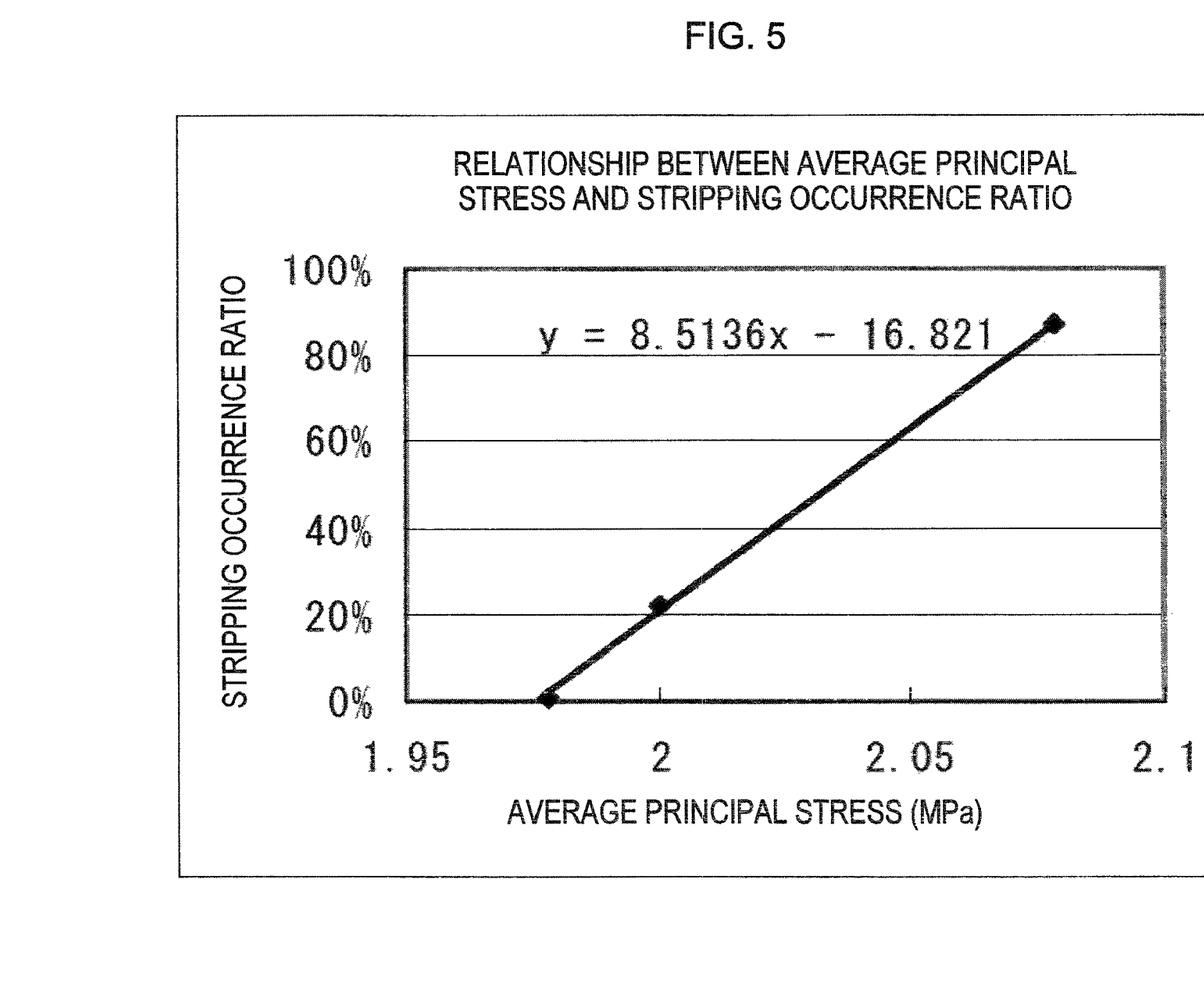
FIG. 5 is a view showing one example of the relationship between an average principal stress and a stripping occurrence ratio according to an embodiment.

On a graph in which the average principal stress is taken along the horizontal axis and the stripping occurrence ratio is taken along the vertical axis, the measured points are shown based on the experimental values, whereby the relationship between the average principal stress and the stripping occurrence ratio can be approximated with a linear function by a least square method, for example. Assuming that the average principal stress is x (MPa) and the stripping occurrence ratio is y(%), the relational expression between the average principal stress and the stripping occurrence ratio in this embodiment is approximated as $$y=8.5136x-16.821$$

The stripping occurrence ratio calculation part 6 calculates the stripping occurrence ratio by substituting the average principal stress calculated by the extracted stress computation part 5 into this relational expression.

The reflow process evaluation device 1 performs the above process from S1 to S6 for each of the plurality of predefined temperature profile.

Now, the temperature profile will be described below. The temperature profile represents how to cool the LSI chip and the substrate that are joined by solder in terms of the cooling time and the cooling temperature.

The cooling of the LSI chip and the substrate is more preferably made by temporarily keeping the temperature at a constant value after cooling to some degree, and then resuming the cooling, than the continuous cooling, because the action of the principal stress is smaller and the stripping is less likely to occur. Also, the action of principal stress is smaller and the stripping is less likely to occur by cooling for a longer time than cooling for a shorter time. However, if it takes longer for the cooling, the production efficiency decreases. Hence, it is required to choose the optimal temperature profile by comparing and considering carefully the stripping occurrence ratio and the cooling time.

Figure 6:
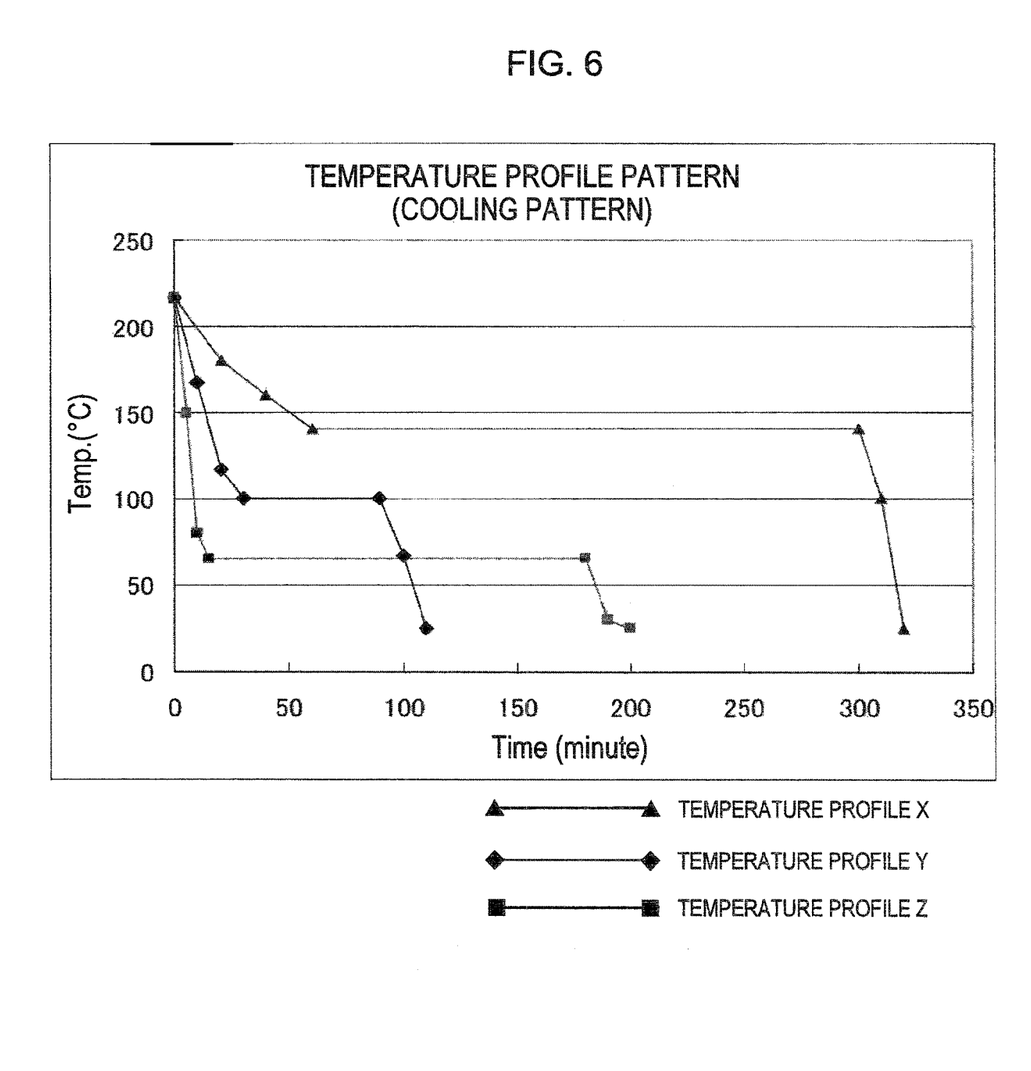
FIG. 6 is a view showing one example of a temperature profile according to an embodiment.

Now, one example of the temperature profile is shown in FIG. 6, in which the temperature profile X is the pattern in which the temperature is cooled to near 140° C. in 60 minutes from the start, kept in an isothermal state for 240 minutes, and then changed to a normal temperature (25° C.) in 25 minutes.

The temperature profile Y is the pattern in which the temperature is cooled to 100° C. in 25 minutes from the start, kept in the isothermal state for about 75 minutes, and then changed to the normal temperature (25° C.) in about 10 minutes. Also, the temperature profile Z is the pattern in which the temperature is cooled to near 60° C. in 15 minutes from the start, kept in the isothermal state for about 170 minutes, and then changed to the normal temperature (25° C.) in about 15 minutes.

Though the above temperature profiles X, Y and Z are only illustrative, a plurality of such temperature profiles are created beforehand. The cooling temperature profile choosing part 7 chooses the optimal temperature profile (i.e., cooling temperature profile having the lower stripping occurrence ratio and shorter cooling time up to the normal temperature) from among the plurality of temperature profiles.

The structural analysis computation part 2 at the above S2 computes the principal stress (accumulated stress) at the final cooling time (325 minutes from the start) for the temperature profile X. For the temperature profiles Y and Z, similarly, the structural analysis computation part 2 computes the principal stress (accumulated stress) at the final cooling time (110 minutes from the start for the temperature profile Y and 200 minutes from the start for the temperature profile Z). The following process up to S6 is performed based on this principal stress (accumulated stress) at the final cooling time.

Returning to the flowchart of FIG. 2, the cooling temperature profile choosing part 7 determines whether or not one of the stripping occurrence ratios calculated at S6 is less than or equal to a predetermined stripping occurrence ratio (e.g., 0.5% or less, and hereinafter 0.5 is a first threshold). If it is less than or equal to the first threshold (S10), the cooling temperature profile choosing part 7 chooses the temperature profile with the concerned stripping occurrence ratio as the optimal temperature profile, and displays the chosen optimal temperature profile and stripping occurrence ratio to the user (S9).

On the other hand, if all the stripping occurrence ratios calculated at S6 are greater than the first threshold (S7), the cooling temperature profile choosing part 7 chooses the temperature profile of a predetermined stripping occurrence ratio or less (e.g., 5% or less, hereinafter 5% is a second threshold), and chooses the temperature profile with the shortest cooling time among the chosen temperature profiles as the optimal temperature profile (S8). And the cooling temperature profile choosing part 7 displays the chosen optimal temperature profile and stripping occurrence ratio to the user (S9).

The reflow process evaluation device 1 may not make the determination by comparison between the stripping occurrence ratio and the first threshold, but may proceed to S8 after the end of processing at S6 for all the temperature profiles.

Figure 7:
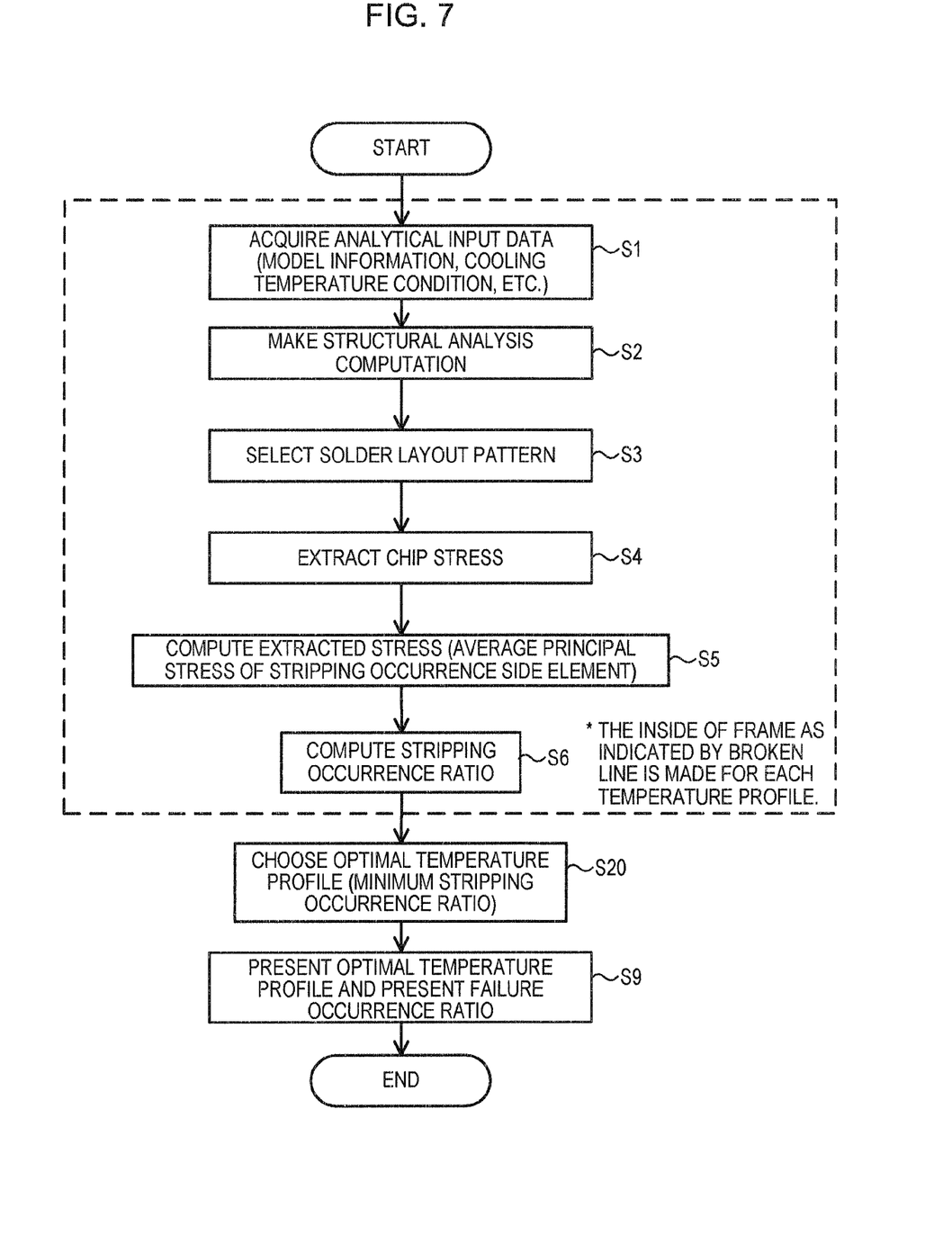
FIG. 7 is a flowchart showing one example of a process for the reflow process evaluation device (selecting the temperature profile at the minimum stripping occurrence ratio) according to an embodiment.

Though the above-described process (from S7 to S10) of the cooling temperature profile choosing part 7 makes the determination by comparing and considering carefully the stripping occurrence ratio and the cooling time, the cooling temperature profile choosing part 7 may choose the temperature profile with the minimum stripping occurrence ratio as the optimal temperature profile from among the plurality of predefined temperature profiles. A process for choosing the minimum stripping occurrence ratio is shown in a flowchart of FIG. 7. In FIG. 7, the process is the same as above described, except for S20, and not described here (see FIG. 2).

The cooling temperature profile choosing part 7 calculates the stripping occurrence ratio for each of the plurality of predefined temperature profiles (from S1 to S6), chooses the temperature profile with the minimum stripping occurrence ratio as the optimal temperature profile (S20), and displays the chosen optimal temperature profile and stripping occurrence ratio to the user (S9).

In this embodiment, the package of a certain stripping occurrence ratio or less can be designed at an LSI package design stage.

Also, in this embodiment, the temperature profile with the minimum stripping occurrence ratio among the plurality of temperature profiles, which has a method of cooling to be least fragile, can be selected.

Further, in this embodiment, even for the already designed LSI package, the stripping occurrence ratio can be decreased by changing the temperature profile.

It should be noted that the stress calculation part corresponds to the structural analysis computation part 2, the solder layout selection part 3, the chip stress extraction part 4 and the extracted stress computation part 5 in this embodiment The rupture occurrence ratio computation part corresponds to the stripping occurrence ratio calculation part 6 in this embodiment. Also, the temperature profile choosing part corresponds to the cooling temperature profile choosing part 7.

What is claimed is:

1. A reflow process evaluation device comprising:
a stress calculation part for calculating an average principal stress acting on a joint portion of a chip by averaging a principal stress acting on the joint portion with a number of electrodes of the chip, wherein a principal stress occurs when the chip and a substrate are joined by solder with a reflow method; and
a rupture occurrence ratio computation part for computing an occurrence ratio at which the joint portion ruptures based on a relational expression between the occurrence ratio and the average principal stress acting on the joint portion and the average principal stress calculated by the stress calculation part.

2. The reflow process evaluation device according to claim 1, wherein the stress calculation part calculates the average principal stress corresponding to each temperature profile, based on at least one temperature profile indicating the relationship between the cooling time and the cooling temperature for cooling the chip and the substrate joined by solder, and the rupture occurrence ratio computation part computes the occurrence ratio corresponding to each temperature profile based on the average principal stress calculated by the stress calculation part.

3. The reflow process evaluation device according to claim 2, further comprising a temperature profile choosing part for choosing a predetermined temperature profile based on the occurrence ratio corresponding to each of the plural temperature profiles calculated by the rupture occurrence ratio computation part.

4. A reflow process evaluation method comprising:
calculating an average principal stress acting on a joint portion of a chip by averaging a principal stress acting on the joint portion with a number of electrodes of the chip, wherein a principal stress occurs when the chip and a substrate are joined by solder with a reflow method; and
computing an occurrence ratio at which the joint portion ruptures based on a relational expression between the occurrence ratio and the average principal stress acting on the joint portion and the calculated average principal stress.

* * * * *